United States Patent [19]
Pham

[11] Patent Number: 6,070,588
[45] Date of Patent: Jun. 6, 2000

[54] BLADDER CONTROL DEVICE RETAINER AND METHOD

[75] Inventor: Tu T. Pham, San Antonio, Tex.

[73] Assignee: HK Medical Technologies Incorporated, San Antonio, Tex.

[21] Appl. No.: 09/246,331

[22] Filed: Feb. 9, 1999

Related U.S. Application Data

[63] Continuation of application No. 08/946,761, Oct. 8, 1997, Pat. No. 5,871,016.

[51] Int. Cl.[7] .......................................................... A61F 5/48
[52] U.S. Cl. .................................. 128/885; 128/DIG. 25; 600/29
[58] Field of Search .................................... 128/885, 886, 128/DIG. 25; 600/29–31

[56] References Cited

U.S. PATENT DOCUMENTS

| | | | |
|---|---|---|---|
| 3,628,530 | 12/1971 | Schwartz | 128/130 |
| 3,812,841 | 5/1974 | Isaacson | 128/DIG. 25 |
| 4,246,896 | 1/1981 | Horne, Jr. et al. | 128/130 |
| 4,553,533 | 11/1985 | Leighton | 128/1 R |
| 4,679,546 | 7/1987 | van Waalwijk van Doorn et al. | 128/1 R |
| 4,969,474 | 11/1990 | Schwarz | 128/885 |
| 5,041,092 | 8/1991 | Barwick | 604/104 |
| 5,123,428 | 6/1992 | Schwarz | 128/885 |
| 5,140,999 | 8/1992 | Ardito | 128/885 |
| 5,618,257 | 4/1997 | Kulisz | 600/29 |
| 5,671,755 | 9/1997 | Simon | 128/885 |
| 5,701,916 | 12/1997 | Kulisz et al. | 128/885 |

FOREIGN PATENT DOCUMENTS

WO 96/18431   6/1996   WIPO.

*Primary Examiner*—Michael A. Brown
*Attorney, Agent, or Firm*—Crompton, Seager & Tufte, LLC

[57] ABSTRACT

A device, system and method for treating female urinary incontinence is provided. A flexible sheath having distally deployed wings and proximal retainer contains a flow control valve unit within. The wings can be tucked into side access holes to reduce the profile of the sheath for insertion distally into a female urethra. Once inserted sufficiently distally into a female urethra, the wings can be deployed by inserting the flow control valve within sufficiently far to force the tucked wings out of the constraining access holes.

21 Claims, 8 Drawing Sheets

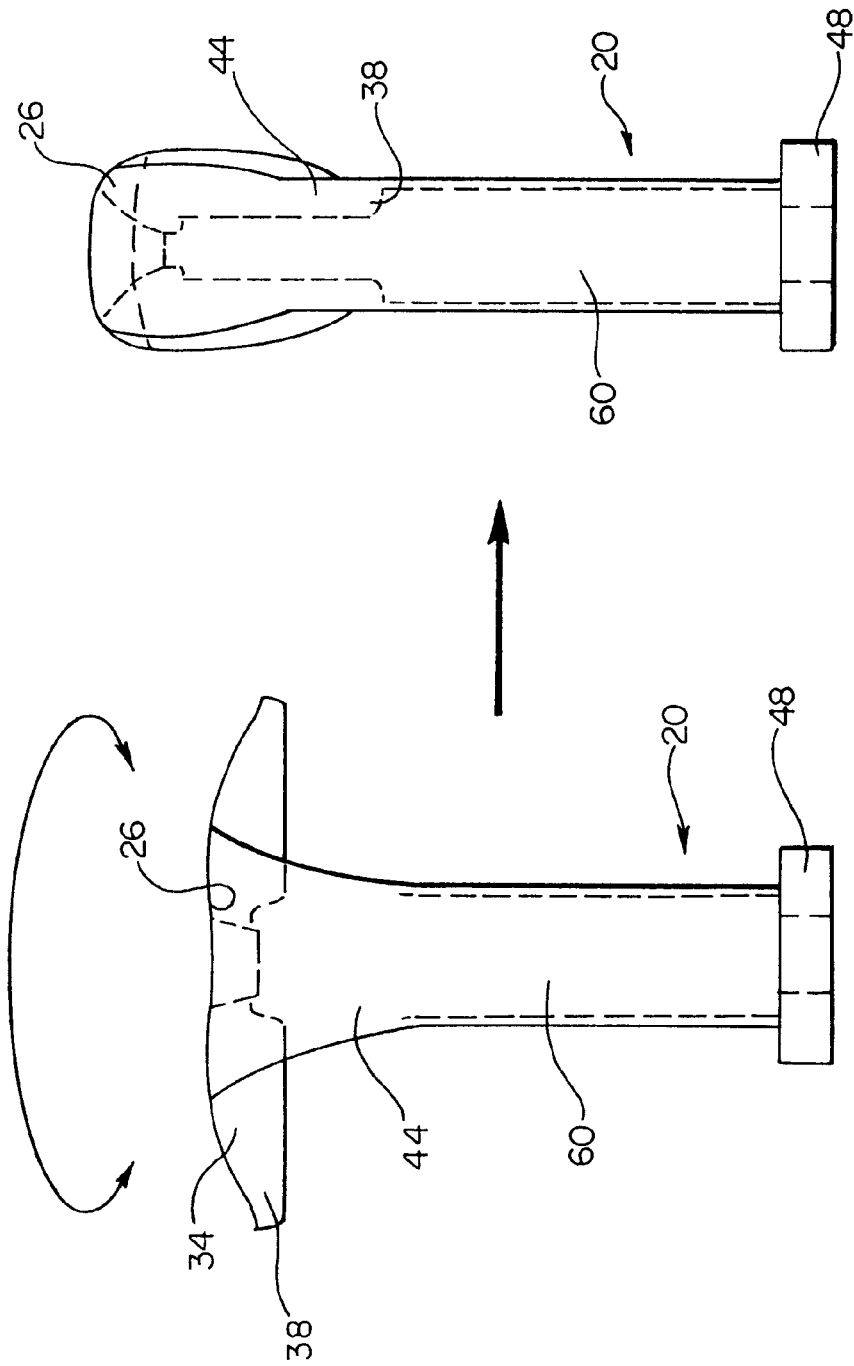

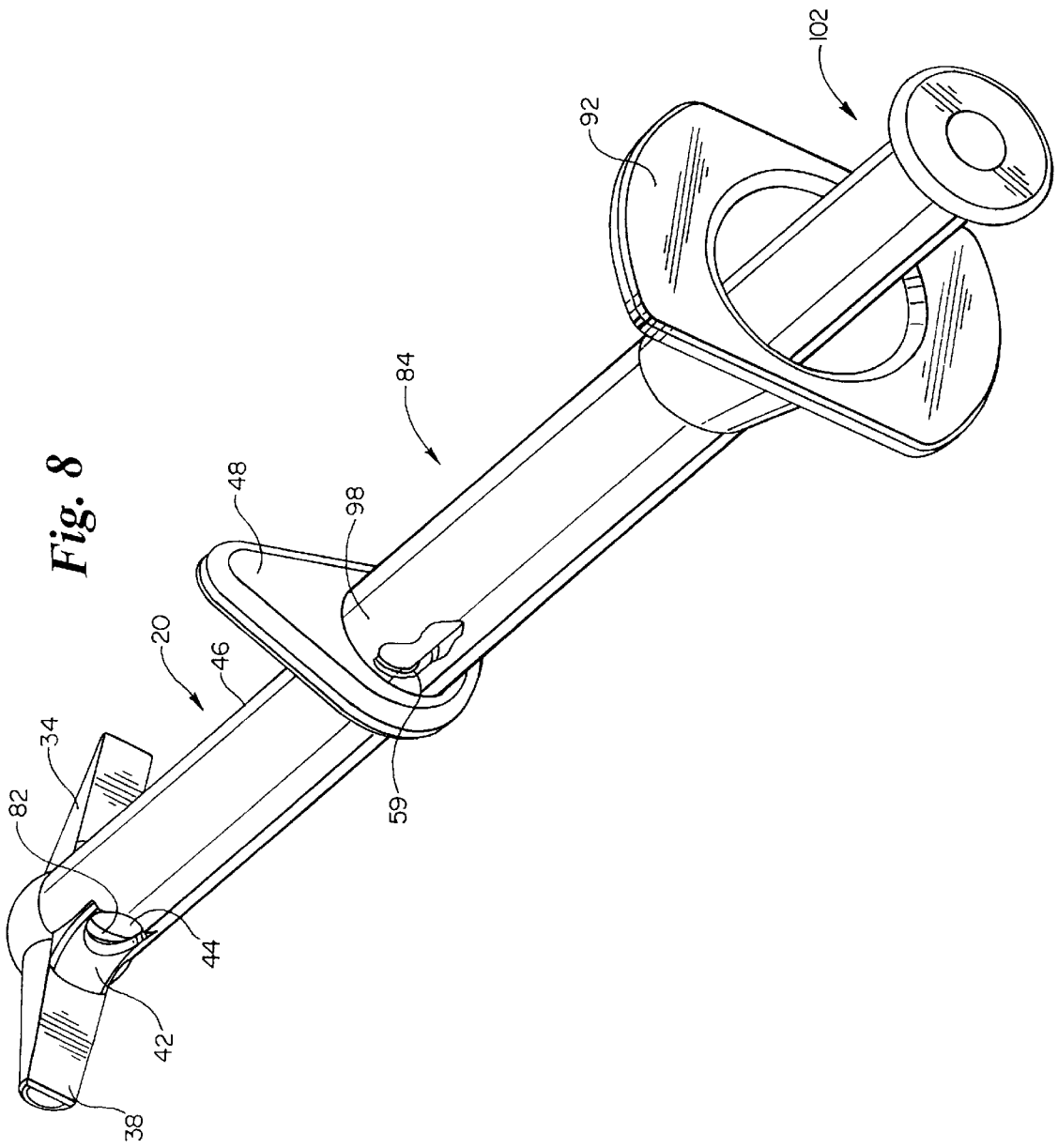

BLADDER CONTROL DEVICE RETAINER AND METHOD

This application is a continuation of copending application Ser. No. 08/946,761, filed Oct. 8, 1997 now U.S. Pat. No. 5,891,016.

RELATED APPLICATIONS

The present invention is related to U.S. application Ser. No. 08/515,920 filed on Aug. 16, 1995, entitled INTRAURETHRAL BLADDER CONTROL DEVICE WITH RETAINER APPARATUS and U.S. application Ser. No. 08/515,564 filed on Aug. 16, 1995, entitled BLADDER CONTROL INSERTION APPARATUS AND METHOD.

FIELD OF THE INVENTION

The present invention relates generally to a device, system and method for treating female urethral incontinence. Specifically, a flexible sheath having deployed wings and flow control valve assembly within is provided as well as a system and method for inserting the sheath.

BACKGROUND OF THE INVENTION

Urinary incontinence, in both males and females, is a significant medical problem. The use of bladder flow control devices, sometimes referred to as artificial sphincters or prosthetic urethral valves, is well known. Bladder flow control devices may be required due to loss of control or removal of the urinary sphincter muscle. The use of such intraurethral valve apparatus and general knowledge in the field of art can be evidenced by, for example, U.S. Pat. Nos. 4,553,533; 4,679,546; 4,969,474; 5,123,428 and 5,140,999.

One goal in the design of such devices is the safe and secure retention of the bladder control or valve device in the female urethra. It is desirable to have the placement of the bladder control apparatus in the urethra performed easily and nonsurgically. It is important that the device be securely retained once placed in the urethra. It is also important that the device be simple and inexpensive to manufacture, allowing for wide-spread adoption and use. Optimally, device surfaces exposed to the human body would be formed of polymeric materials, to lessen chances of inflammation in patients susceptible to irritation caused by contact with metals. A device should have both soft, flexible surfaces for retaining the device and strong materials within the valve portion. Various prior art devices have not met all of these criteria.

SUMMARY OF THE INVENTION

The present invention includes a device, system and method for dealing with female urinary incontinence. A flexible sheath is provided for enclosing a flow control valve unit within. The sheath can include distal wings which are flexible and are capable of being tucked within side access holes within the sheath. The sheath also can include a proximal retainer for preventing unwanted distal movement through the female urethra into the bladder. The distal wings can have an outwardly extending position and a proximally, tucked, extending position. The wings are inserted into the tucked position and are deployed to the outwardly extending position after the sheath is advanced within the female urethra. The wings are deployed by distally advancing the flow control valve unit within the sheath, dislodging the wings from their tucked position.

In a preferred embodiment, the sheath wings are biased to assume a first, outwardly extended position. The wings are preferably elastically hinged to the distal sheath portion and are formed integrally with the sheath. A preferred sheath is formed integrally of a single material. The sheath can include internal distal stops and internal proximal lock cavities to arrest distal and proximal movement of a flow control valve unit contained within, respectively.

A system according to the present invention can include a flow control valve unit, a tubular extender having a lumen therethrough, the extender having a distal portion, an intermediate portion and a proximal portion, with the distal portion adapted to be slidably received by the flow control valve unit proximal portion, and the proximal portion adapted to be slidably received by a flow control lock unit distal portion. The tubular extender intermediate portion is preferably to large to be received within the flow control valve unit portion and can have an outer profile sufficient to provide a tight, friction fit within the sheath interior. A tubular case is also provided and includes a distal portion, a proximal portion and a lumen therethrough, with the tubular case distal end being adapted to be inserted and releasably secured to the sheath proximal end. The present invention also provides a tubular plunger adapted to be received by the flow control lock unit proximal portion, thereby allowing the flow control lock unit to be advanced distally using the plunger.

In use, the case can be attached to the sheath proximal end, the sheath distal wings tucked into a longitudinal proximal position, and the locking mechanism assembly, including a flow control valve unit, can be releasably secured to the plunger distal end. Plunger and attached locking mechanism can then be advanced distally within the case and sheath, stopping short of forcing the tucked wings out of the access holes receiving them. After pre-dilating the urethra, the case can be used to advance the sheath within the urethra until the proximal retainer is forced against the urethral labial region, whereupon the plunger can be advanced further distally, forcing the contained flow control valve unit distally within the sheath, thereby forcing the wings outwardly into a deployed position. The plunger can be used to further advance the locking mechanism assembly until the locking tabs lock the assembly into position within the sheath. The case and plunger may then be retracted.

BRIEF DESCRIPTION OF THE DRAWINGS

FIG. 7a is a cross sectional view of the sheath of FIG. 1, shown before the wings are tucked within the sheath apertures; and FIG. 7b is a side, cross sectional view of the sheath of FIG. 7a shown after the wings are tucked within the side access holes;

FIG. 8 is a perspective view of the sheath, case, and plunger of FIG. 6, where the plunger has advanced the locking mechanism distally sufficiently far to deploy the wings.

DETAILED DESCRIPTION OF THE PREFERRED EMBODIMENTS

Figure 1:
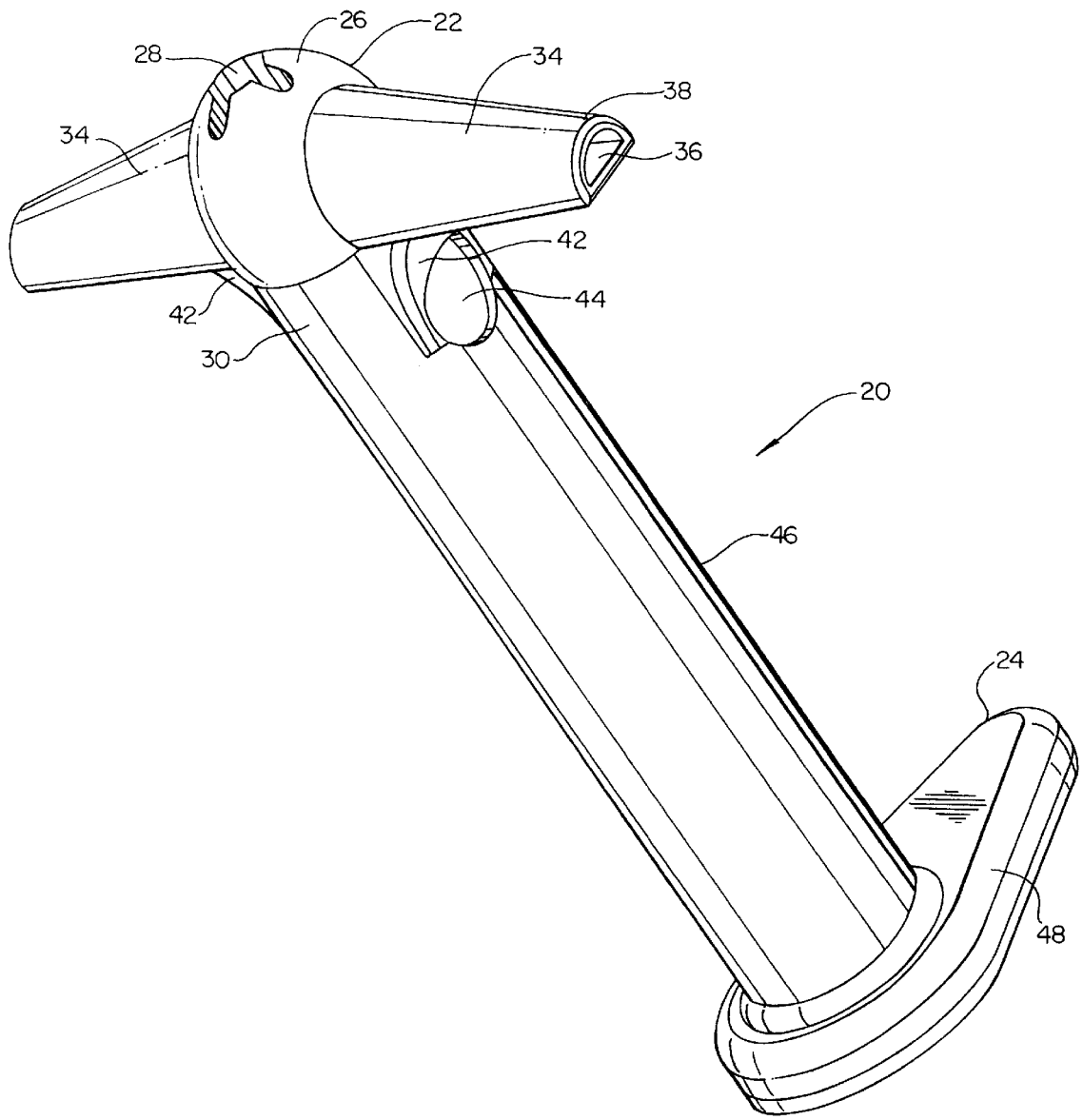
FIG. 1 is a perspective view of an intraurethral sheath.

FIG. 1 illustrates an intraurethral sheath 20 having a distal region 22 and a proximal region 24, where distal region 22 is designed for insertion into a female urethra, into the bladder of a patient. Sheath 20 can contain a flow control valve unit within (not shown in FIG. 1) and includes a pair of distal wings or members 34 and a proximal retainer 48. Wings 34 serve to prevent proximal motion of sheath 20 out of the patient by resting on the bladder floor. Proximal retainer 48 serves to prevent distal motion of sheath 20 into the patient by lying against the urethral labial. Sheath 20 has a lumen therethrough extending from a distal orifice 28 through a sheath tube 46 and exiting proximally at proximal retainer 48. A distal tip 26 preferably has a rounded shape to ease insertion through the urethra. Tube 46 has distal walls 30 having distal access holes or apertures 44 therethrough and wing braces 42 proximal of wings 34. Wing braces 42 can serve to bias wings 34 in the outwardly extending position illustrated in FIG. 1. Wings 34 have an outer extent 38, preferably including a wing hollow region 36, for ease in holding wings 34. Wing outer extents 38 can be bent or folded proximally, and inserted into distal access holes 44. In this way, wings 34 are forced to assume a proximal orientation. In this position, wing outer extents 38 are suspectable to being forced or popped out of distal access holes 44 by a member traveling distally within tube 46. Sheath 20 is preferably formed integrally of a single material, such as medical grade silicone or rubber. A preferred method of making sheath 20 is injection molding.

Figure 2:
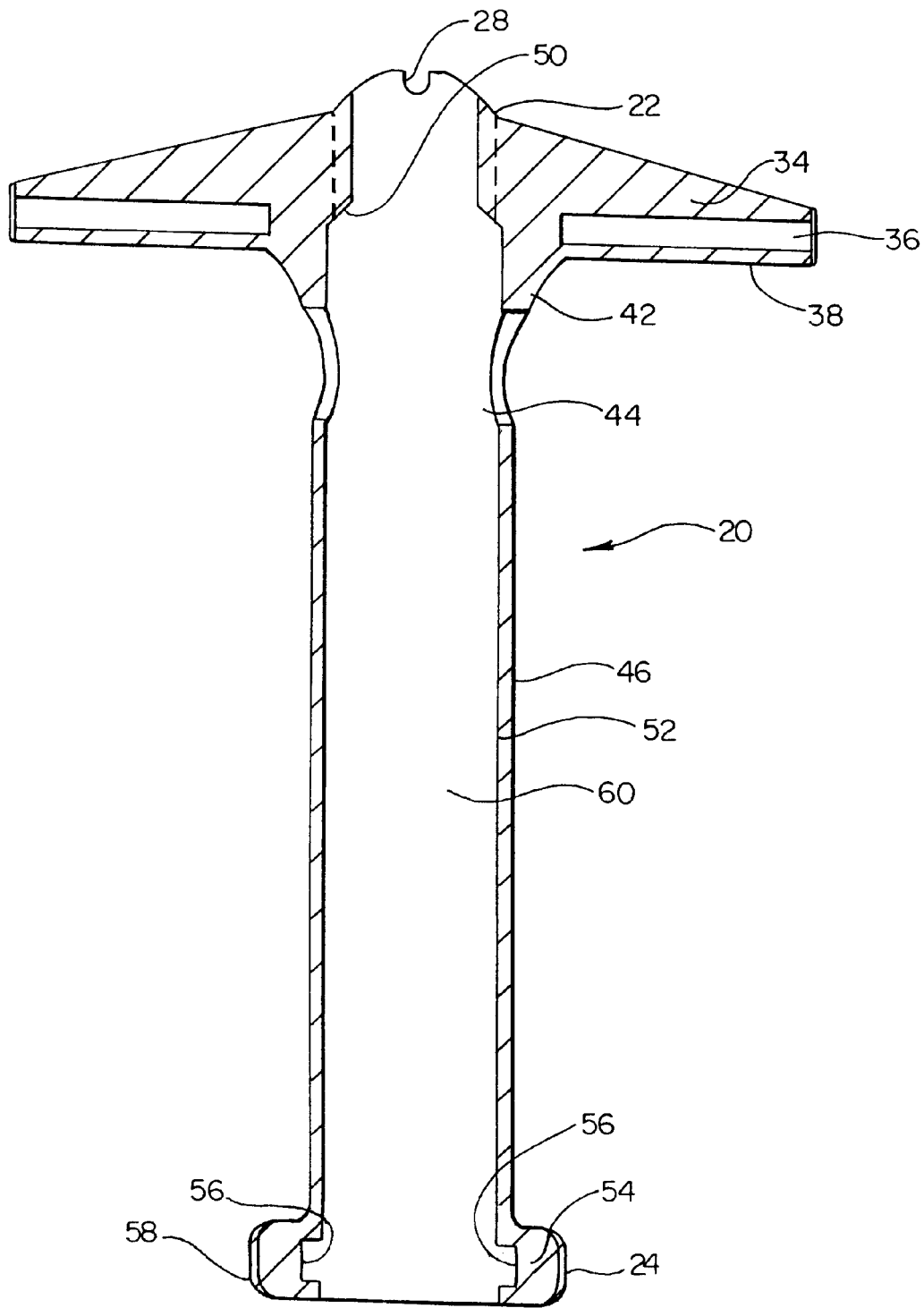
FIG. 2 is a cross sectional view taken through the longitudinal axis of the intraurethral sheath of FIG. 1.

Single piece construction simplifies assembly and reduces the possibility of any sheath components separating during residence in the patient. Referring now to FIG. 2, sheath 20 is shown in cross section. Tube 46 includes a tube wall 52 defining a central lumen 60, providing a fluid flow channel from distal orifice 28 to a proximal orifice 58 in proximal region 24. Proximal region 24 includes a proximal lock 54 having recesses or cavities 56. Recesses 56 receive lock tabs for holding a flow control valve unit in place (not shown in FIG. 2). A distal stop 50 lies in distal region 22 for arresting the distal movement of a contained flow control valve unit. Tube walls 52 are preferably formed of an elastomeric material such that a tubular flow control valve unit inserted within lumen 60 is partially held in position by a friction fit between the elastically stretched tube walls 52 and the outside walls of the inserted flow control valve unit.

Figure 3:
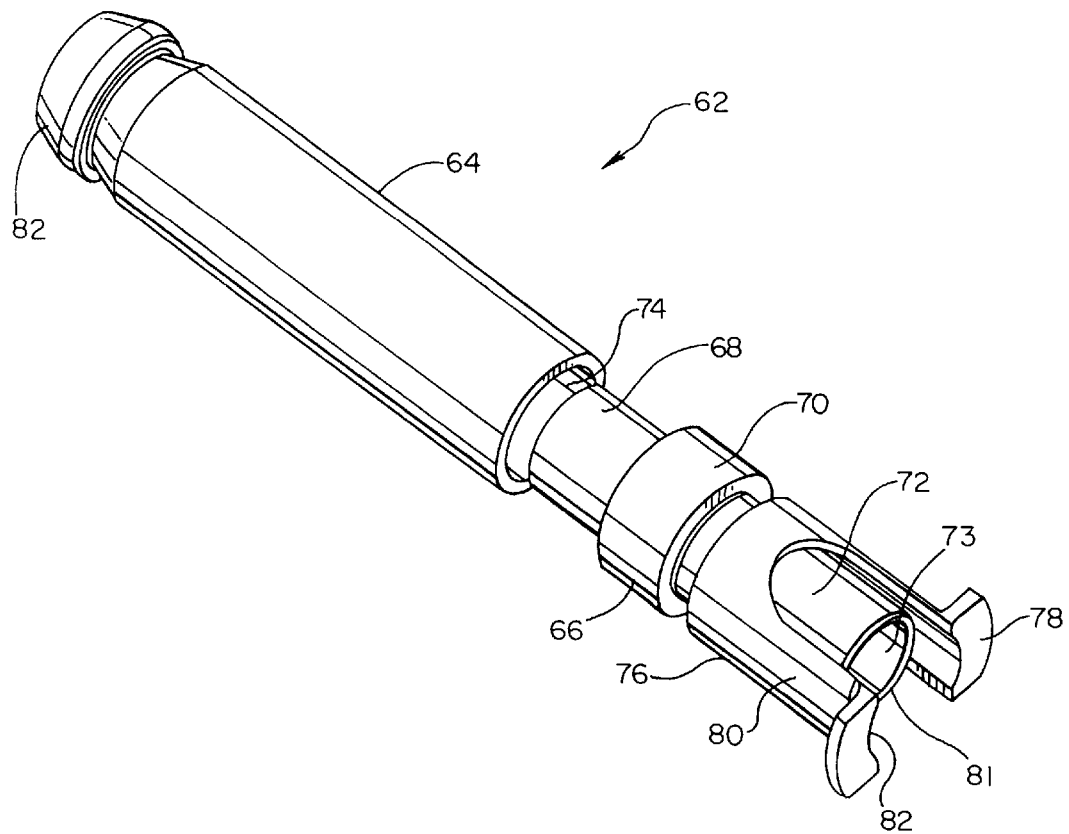
FIG. 3 is a perspective, exploded view of locking mechanism assembly for insertion into the sheath of FIG. 1.

Referring now to FIG. 3, a locking mechanism assembly 62, suitable for insertion within sheath 20 is illustrated. Locking mechanism assembly 62 includes a distal tip 82, a flow control valve unit 64, a tubular extender 66, and a proximal lock 76. Flow control valve unit distal tip 82 serves to provide a tight fit against distal stop 50 within sheath lumen 60, as illustrated in FIG. 1. Distal tip 82 is preferably formed of medical grade steel. Tubular flow control valve unit 64 can be a flow control unit as disclosed in co-pending U.S. application Ser. No. 08/515,920 filed on Aug. 16, 1995, entitled INTRAURETHRAL BLADDER CONTROL DEVICE WITH RETAINER APPARATUS, herein incorporated by reference. Flow control valve unit 64 includes a valve mechanism for controlling the flow of urine through flow control valve unit 64. A proximal lumen region 74 in flow control valve unit 64 is adapted to receive an extender distal region 68 sufficiently tightly such that fluid flow is constrained within the lumen of tubular extender 66. An extender intermediate portion 70 is preferably greater in outside diameter than extender distal portion 68 and can serve to provide both a friction fit and a seal between the outside of intermediate portion 70 and the interior of sheath tube wall 52. Extender 66 includes a proximal portion 72 having a proximal orifice 73. Extender 66 is preferably formed of medical grade rubber, in a single piece, by a method such as molding.

Extender proximal portion 72 is adapted to receive locking mechanism assembly lock 76 thereover. In a preferred embodiment, extender proximal portion 72 fits loosely within lock 76. Lock 76 includes walls 80, and has a proximal slotted portion 82. Locking tabs 78 are attached to the proximal portion of walls 80. Lock tabs 78 may be squeezed together, thereby temporary decreasing the profile of lock 76 for insertion within sheath 20. Lock 76 can be formed of a material such as medical grade plastic. As may be seen from inspection of FIG. 3, flow control valve unit distal tip 82 can serve to arrest distal movement, while lock tabs 78 can serve to arrest proximal movement of flow control valve unit 64.

Figure 4:
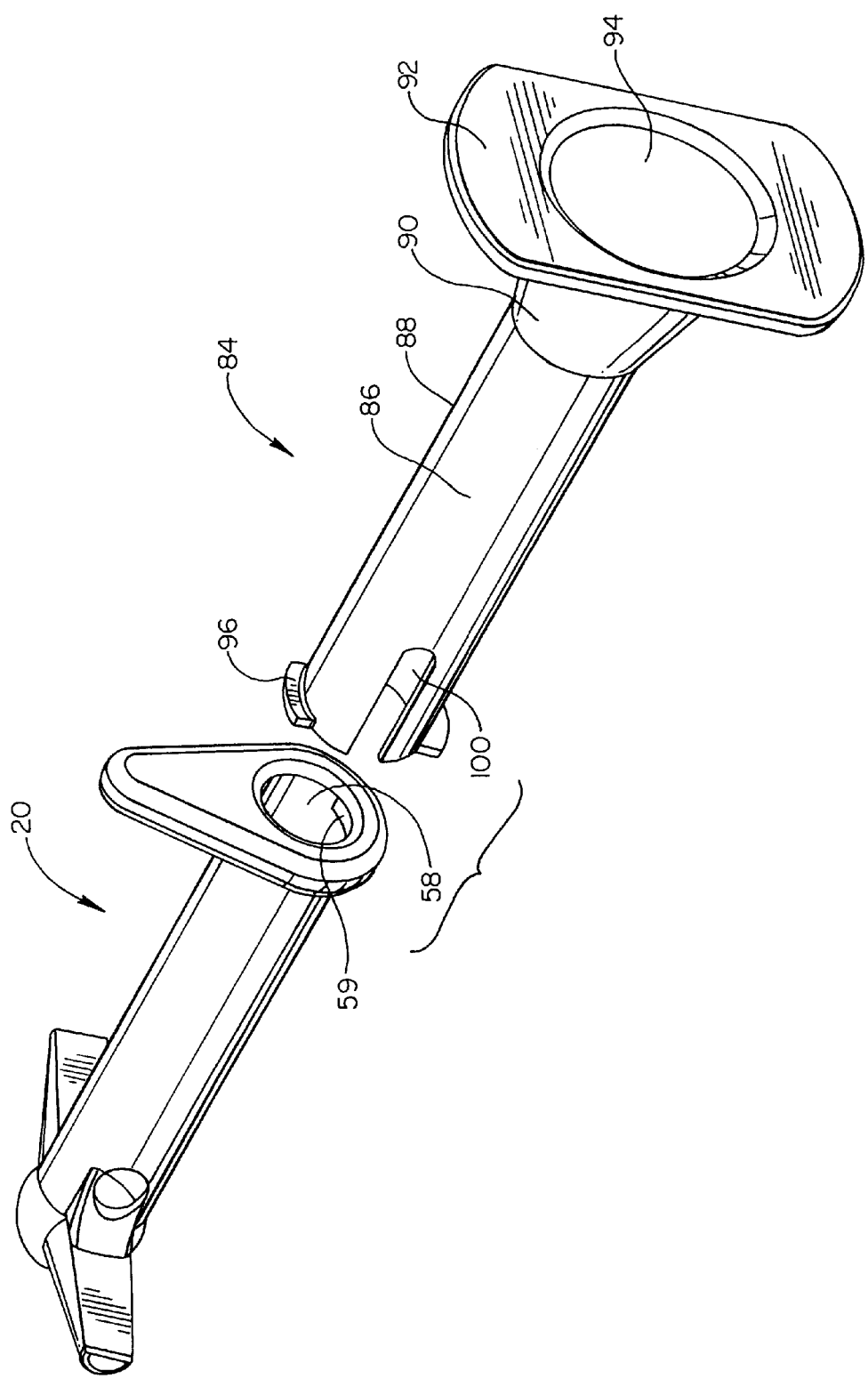
FIG. 4 is a perspective view of the sheath of FIG. 1 and a tubular case for inserting the sheath within the female urethra.

Referring now to FIG. 4, a tubular case 84 is illustrated, extending from distal lock tabs 96 to proximal base 92. Case 84 is preferably formed of a material such as medical grade plastic. Case distal slots 100 lie between opposed distal lock tabs 96, allowing for reducing the outer profile case 84 distal end, by squeezing together case distal lock tabs 96. Case 84 includes a tubular body 86 having tube walls 88 and a proximal tapered portion 90 extending to proximal base 92. Case 84 includes a lumen therethrough exiting proximally at proximal orifice 94. Within orifice 58 of sheath 20, sheath proximal locks 59 are positioned, for securing the inserted distal end of case 84. Case 84 allows for more easily handling sheath 20 and allows disposing a flow control valve unit within sheath 20.

Figure 5:
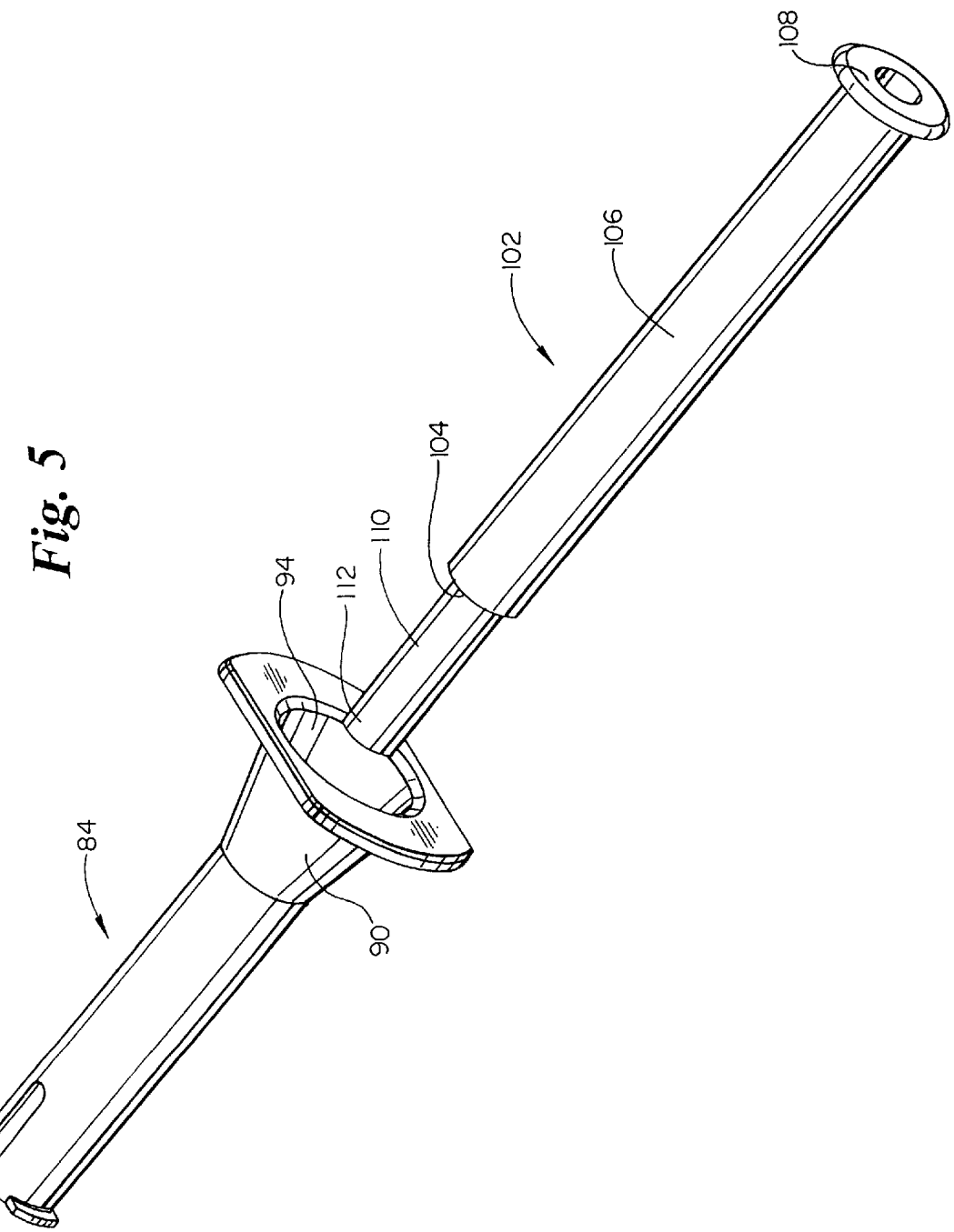
FIG. 5 is a perspective view of the tubular case of FIG. 4 and a plunger adapted to be slidably received by the case.

Referring now to FIG. 5, a plunger 102 is illustrated, having a tubular body 106, extending from a distal end 112 through a distal narrowed portion 110 and a plunger stop 104, terminating in a proximal thumb rest 108. Plunger 102 is preferably formed of a plastic material such as medical grade plastic. Plunger 102 is adapted to be received within proximal orifice 94 and proximal tapered portion 90 of case 84. Distal narrowed portion 110 is suitable for mounting to locking mechanism assembly 62 of FIG. 3, for insertion of assembly 62 through case 84 and sheath 20.

Figure 6:
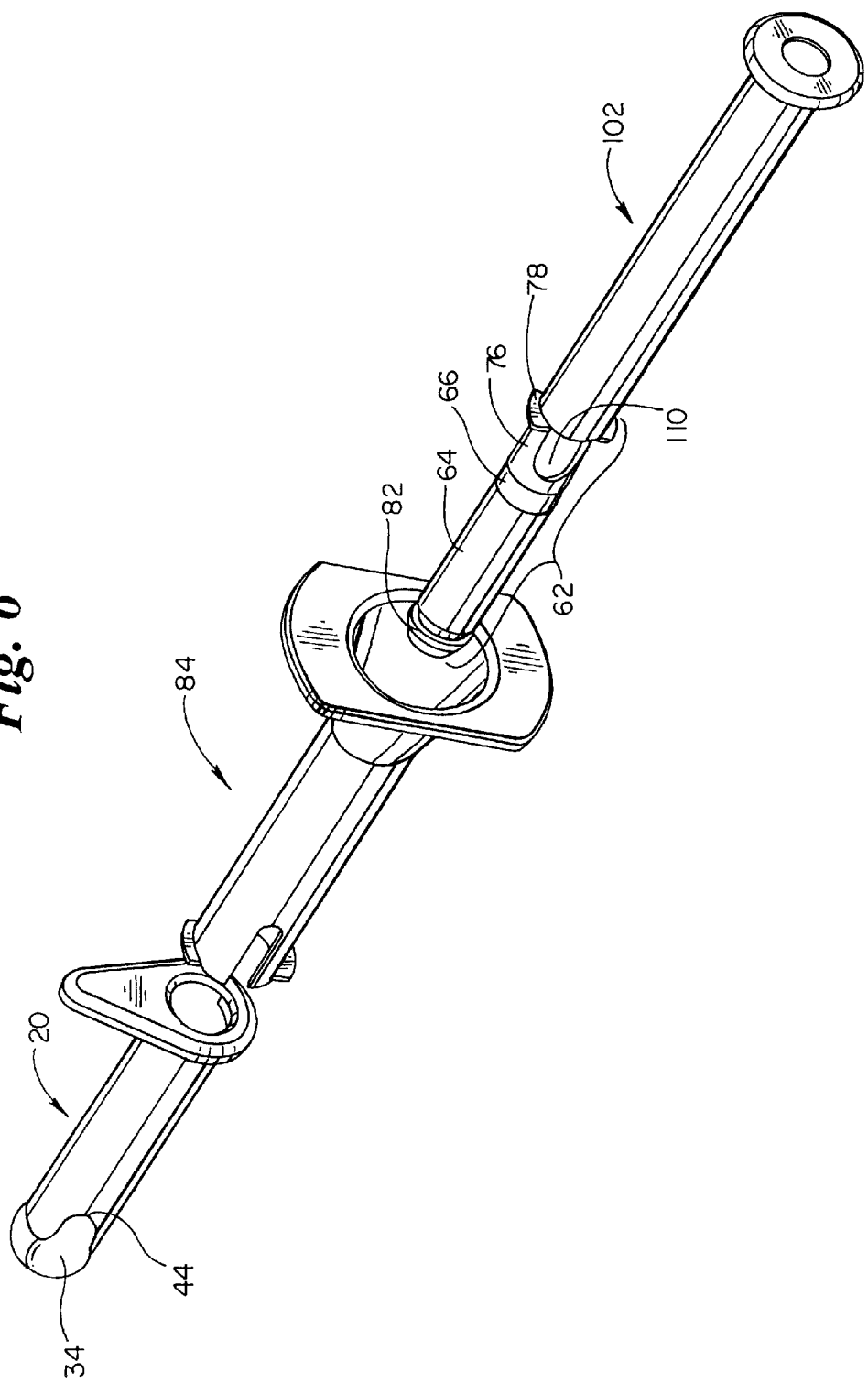
FIG. 6 is a perspective view of the sheath of FIG. 1, the tubular case of FIG. 4, and the locking assembly of FIG. 3 removably secured to the plunger of FIG. 5.

Referring now to FIG. 6, locking mechanism assembly 62 is shown mounted on distal narrowed portion 110 of plunger 102. Locking mechanism assembly 62, shown assembled, includes distal tip 82, flow control valve unit 64, tubular extender 66, proximal lock 76, having proximal lock tabs 78. Wings 34 are shown tucked into access hole 44, in proper position for insertion within the female urethra.

Referring now to FIG. 7a, sheath 20 is shown with wings 34 outwardly extended. Distal tip 26 may be seen to have a conical shape, being somewhat larger distally than proximally. Outer wings extents 38 may be tucked into access holes 44, resulting in sheath 20 having the configuration shown in FIG. 7b. In FIG. 7b, wing outer extents 38 are tucked within access holes 44, in positions suitable for insertion within the female urethra. Inspection of FIG. 7 shows that wing outer extents 38 may also be dislodged by a tubular member advancing distally within sheath lumen 60.

Referring now to FIG. 8, case 84 has been inserted and locked into sheath 20, and plunger 102 has been inserted distally within case 84. FIG. 8 illustrates sheath 20, case 84 and plunger 102 in the position reached after sheath 20 has been advanced distally into the female urethra and plunger 102 has been advanced distally sufficiently far to deploy wings 34. Plunger 102 has advanced the locking mechanism assembly sufficiently far to press distal tip 82 against tucked wings 34, forcing wings 34 out of access hole 44. Outwardly extending wings 34 are biased into a transverse relationship with sheath tube 46 by braces 42. Case locking tabs 96 have been advanced within sheath proximal orifice 58, best illustrated in FIGS. 4 and 8. When plunger 102 has been advanced to its distal-most extent, locking mechanism assembly distal tip 82 is forced against distal stop 50, best illustrated in FIG. 2. In this distal-most position, locking mechanism assembly proximal lock tabs 78, as illustrated in FIG. 6, lock within locking cavities 56 as illustrated in FIG. 2. With locking mechanism assembly distal tip 82 firmly lodged against sheath distal tip 50, as illustrated in FIG. 2, fluid flow is channeled through the interior of the inserted locking mechanism assembly rather than around the exterior of the locking mechanism assembly. Extender intermediate portion 70, as illustrated in FIG. 3, serves to provide a water tight seal when forced within preferably elastic tube wall 52, as illustrated in FIG. 2. The water tight fit prevents flow through access holes 44, which could otherwise bypass the contained flow control valve unit.

In use, locking mechanism assembly 62 can be preassembled as illustrated in FIG. 3. Tubular extender 66 can be forced into a tight fit with flow control valve unit proximal lumen portion 74. Locking mechanism assembly lock 76 may be slid over tubular extender proximal portion 72. Plunger 102 may then have distal narrowed portion 110 inserted within lock 76 and locking mechanism assembly lumen 81, as illustrated in FIG. 6. Wings 34 may be forced to lie proximally and tucked into access holes 44, as illustrated in FIGS. 6, 7a and 7b. Case distal end 98 can be inserted within sheath proximal lock 59 by squeezing together distal lock tabs 98 and advancing tabs 96 within sheath proximal orifice 98, thereby securing case 84 to sheath 20. This brings case 84 and sheath 20 into the connected configuration as shown in FIG. 8, but with wings 34 still tucked and plunger 108 not yet inserted. With case and sheath attached, plunger 102 and locking mechanism assembly 62 are advanced distally together within case 84, proceeding into sheath 20, but stopping short of the point where locking mechanism assembly distal tip 82 would contact tucked wings 34. The resulting system resembles the system in FIG. 8, but with wings 34 still tucked into access holes 44 and plunger 102 not advanced as far distally. Sheath 20 is now prepared for insertion.

The foregoing procedure can be preformed away from the patient. The urethra of the patient should be pre-dilated and lubricated. Case 84 can be used to distally advance sheath distal tip 26 within the female urethra and into the bladder of the patient. Once sheath proximal retainer 48 is pressed against the urethral labial region, plunger 102 can be advanced distally forcing locking mechanism assembly distal tip 82 distally against tucked wing outer extents 38, thereby forcing them out of access holes 44. Deployed wings 34 thereby are outwardly extended and provide resistance to forces which would tend to dislodge sheath 20 proximally out of the urethra. Plunger 102 can then be advanced even further distally, to insure that locking mechanism assembly lock tabs 78 are received within sheath proximal lock cavities 56, best visualized with reference to FIGS. 2 and 3. With wings 34 deployed and locking mechanism assembly 62 locked in place, plunger 102 can be retracted proximally from within case 84 and case 84 can be disconnected from sheath 20 by squeezing case distal ends 98 and retracting case locking tabs 96.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of assembling a urethral indwelling device for selectively draining urine from a bladder, comprising the steps of:

providing a bladder drainage shaft having a proximal end, a distal end, and defining an elongated cavity for draining urine from a bladder positioned at the distal end thereof;

providing a means for controlling urine flow adapted to be received in the elongated cavity of the bladder drainage shaft;

providing a tubular case having a distal end, a proximal end, and a lumen extending therebetween;

providing a plunger having a distal end, a proximal end, and a body portion extending therebetween;

inserting the distal end of the tubular case into the elongated cavity of the bladder drainage shaft;

inserting the means for controlling urine flow into the lumen of the tubular case;

inserting the distal end of the plunger into the lumen of the tubular case;

urging the plunger toward the distal end of the tubular case until the distal end of the plunger contacts the means for controlling urine flow;

urging the means for controlling urine flow through the lumen of the tubular case and into the elongated cavity of the bladder drainage shaft; and removing the tubular case from the elongated cavity of the bladder drainage shaft.

2. The method of claim 1, wherein the step of urging the means for controlling urine flow through the lumen of the tubular case and into the elongated cavity of the bladder drainage shaft includes the step of applying a force to the proximal end of the plunger.

3. The method of claim 2, wherein the step of applying a force to the proximal end of the plunger includes pressing on the distal end of the plunger with a thumb.

4. The method of claim 1, wherein the plunger includes a thumb rest disposed at the distal end thereof.

5. The method of claim 1, wherein the lumen of the tubular case is adapted to slidingly receive the means for controlling urine flow.

6. The method of claim 1, wherein the plunger is adapted to be slidably received within the lumen of the tubular case.

7. The method of claim 1, wherein the bladder drainage shaft is comprised of an elastomeric material.

8. The method of claim 1, wherein the bladder drainage shaft is comprised of silicone rubber.

9. The method of claim 1, wherein the bladder drainage shaft is comprised of rubber.

10. The method of claim 1, wherein the bladder drainage shaft further includes an orifice proximate the distal end thereof.

11. The method of claim 1, wherein the bladder drainage shaft further includes an orifice proximate the distal end thereof, the orifice being in fluid communication with the elongated cavity of the bladder drainage shaft.

12. The method of claim 1, wherein the elongated cavity of the bladder drainage shaft further includes a recess proximate the proximal end thereof.

13. A method of assembling a urethral indwelling device for selectively draining urine from a bladder, comprising the steps of:
  providing a bladder drainage shaft having a proximal end, a distal end, and defining an elongated cavity for draining urine from a bladder positioned at the distal end thereof;
  providing a means for controlling urine flow adapted to be received in the elongated cavity of the bladder drainage shaft;
  providing a tubular case having a distal end, a proximal end, and a lumen extending therebetween;
  inserting the distal end of the tubular case into the elongated cavity of the bladder drainage shaft;
  inserting the means for controlling urine flow into the lumen of the tubular case;
  urging the means for controlling urine flow through the lumen of the tubular case and into the elongated cavity of the bladder drainage shaft; and
  removing the tubular case from the elongated cavity of the bladder drainage shaft.

14. The method of claim 13, wherein the step of urging the means for controlling urine flow through the lumen of the tubular case and into the elongated cavity of the bladder drainage shaft includes the step of applying a force to the means for controlling urine flow.

15. The method of claim 13, wherein the lumen of the tubular case is adapted to slidingly receive the means for controlling urine flow.

16. The method of claim 13, wherein the bladder drainage shaft is comprised of an elastomeric material.

17. The method of claim 13, wherein the bladder drainage shaft is comprised of silicone rubber.

18. The method of claim 13, wherein the bladder drainage shaft is comprised of rubber.

19. The method of claim 13, wherein the bladder drainage shaft further includes an orifice proximate the distal end thereof.

20. The method of claim 13, wherein the bladder drainage shaft further includes an orifice proximate the distal end thereof;
  the orifice being in fluid communication with the elongated cavity of the bladder drainage shaft.

21. The method of claim 13, wherein the elongate cavity of the bladder drainage shaft further includes a recess proximate the proximal end thereof.

* * * * *